(12) United States Patent
Krause

(10) Patent No.: US 9,801,663 B2
(45) Date of Patent: Oct. 31, 2017

(54) FLEXIBLE SPINE COMPONENTS

(71) Applicant: William R. Krause, Charlottesville, VA (US)

(72) Inventor: William R. Krause, Charlottesville, VA (US)

(73) Assignee: Flex Technology, Inc., Charlottesville, VA (US)

( * ) Notice: Subject to any disclaimer, the term of this patent is extended or adjusted under 35 U.S.C. 154(b) by 0 days.

(21) Appl. No.: 14/859,670

(22) Filed: Sep. 21, 2015

(65) Prior Publication Data

US 2016/0051287 A1 Feb. 25, 2016

Related U.S. Application Data

(63) Continuation-in-part of application No. 12/069,934, filed on Feb. 14, 2008, now Pat. No. 9,138,263.

(Continued)

(51) Int. Cl.
*A61B 17/70* (2006.01)
*A61F 2/44* (2006.01)
(Continued)

(52) U.S. Cl.
CPC ...... *A61B 17/7028* (2013.01); *A61B 17/7029* (2013.01); *A61B 17/7031* (2013.01); *A61F 2/44* (2013.01); *A61B 17/7041* (2013.01); *A61B 2017/564* (2013.01); *A61F 2/4425* (2013.01); *A61F 2002/3055* (2013.01); *A61F 2002/30405* (2013.01); *A61F 2002/30563* (2013.01); *A61F 2002/30566* (2013.01);
(Continued)

(58) Field of Classification Search
CPC ............ A61B 17/7031; A61B 17/7026; A61B 17/7028; A61B 17/7002; A61B 17/7019; A61B 2017/00862; A61F 2/44; A61F 2/442; A61F 2/4425; A61F 2002/443; A61F 2002/5016; A61F 2002/502; A61F 2002/5021
USPC .... 606/246, 254–255, 261; 623/17.15–17.16
See application file for complete search history.

(56) References Cited

U.S. PATENT DOCUMENTS 2,515,366 A * 7/1950 Zublin ............... E21B 7/06
138/120
3,426,364 A 2/1969 Lumb
(Continued)

*Primary Examiner* — Eduardo C Robert
*Assistant Examiner* — Michelle C Eckman
(74) *Attorney, Agent, or Firm* — Kimberly Snead

(57) ABSTRACT

An improved flexible component used for dynamic stabilization of spinal segments for the treatment of vertebrae deformities and injuries and for the replacement of a complete or segment of the body of a vertebra in the spine is described. The flexible component is comprised of a solid, suitable implant material with a longitudinal bore the entire length and an appropriately formed slot which extends spirally around the shaft either continuously or segmentally. The flexible component may be encapsulated, fully or partially, in a suitable implant grade elastomeric resilient material. When used for a dynamic stabilization device, the component is attached to the vertebral bodies by pedicle screws know to those in the art. When used as a vertebral replacement device, attached to the component's opposite ends are members for attachment to the adjacent vertebra that allow for height and angular adjustment.

18 Claims, 14 Drawing Sheets

Related U.S. Application Data

(60) Provisional application No. 60/901,150, filed on Feb. 14, 2007.

(51) Int. Cl.
  *A61F 2/30* (2006.01)
  *A61B 17/56* (2006.01)

(52) U.S. Cl.
  CPC .............. *A61F 2002/30649* (2013.01); *A61F 2002/30841* (2013.01); *A61F 2220/0025* (2013.01); *A61F 2310/00011* (2013.01)

(56) References Cited

U.S. PATENT DOCUMENTS

| | | | |
|---|---|---|---|
| 4,328,839 A * | 5/1982 | Lyons | E21B 17/20 138/120 |
| 4,401,112 A | 8/1983 | Rezaian | |
| 4,554,914 A | 11/1985 | Kapp et al. | |
| 4,599,086 A | 7/1986 | Doty | |
| 4,932,975 A | 6/1990 | Main | |
| 5,092,866 A | 3/1992 | Breard et al. | |
| 5,147,404 A | 9/1992 | Downey | |
| 5,192,327 A | 3/1993 | Brantigan | |
| 5,282,863 A | 2/1994 | Burton | |
| 5,437,669 A | 8/1995 | Yuan | |
| 5,474,555 A | 12/1995 | Puno | |
| 5,571,192 A | 11/1996 | Schonhoffer | |
| 5,702,455 A * | 12/1997 | Saggar | A61F 2/44 623/17.15 |
| 5,776,198 A * | 7/1998 | Rabbe | A61B 17/70 606/247 |
| 6,053,922 A * | 4/2000 | Krause | A61B 17/164 464/78 |
| 6,193,756 B1 * | 2/2001 | Studer | A61F 2/44 623/17.15 |
| 6,293,949 B1 | 9/2001 | Justis | |
| 6,468,276 B1 | 10/2002 | McKay | |
| 6,645,207 B2 | 11/2003 | Dixon | |
| 6,966,910 B2 | 11/2005 | Ritland | |
| 6,989,011 B2 | 1/2006 | Paul | |
| 7,018,379 B2 | 3/2006 | Drewry | |
| 7,083,621 B2 | 8/2006 | Shaolian | |
| 7,413,563 B2 * | 8/2008 | Corcoran | A61B 17/0057 604/523 |
| 7,766,915 B2 * | 8/2010 | Jackson | A61B 17/7028 606/254 |
| 8,123,060 B2 * | 2/2012 | Obergoenner | B65D 9/04 217/65 |
| 8,221,467 B2 * | 7/2012 | Butler | A61B 17/7023 606/255 |
| 8,353,898 B2 * | 1/2013 | Lutze | A61B 17/32002 606/1 |
| 8,376,865 B2 * | 2/2013 | Forster | A61F 2/2427 464/149 |
| 8,382,742 B2 * | 2/2013 | Hermann | A61B 17/1631 606/1 |
| 8,518,084 B2 * | 8/2013 | Biedermann | A61B 17/7028 606/254 |
| 8,591,587 B2 * | 11/2013 | Refai | A61F 2/44 623/17.15 |
| 9,468,359 B2 * | 10/2016 | Weisshaupt | A61B 1/00071 |
| 2002/0128715 A1 | 9/2002 | Bryan | |
| 2003/0109880 A1 * | 6/2003 | Shirado | A61B 17/7028 606/328 |
| 2004/0236328 A1 * | 11/2004 | Paul | A61B 17/7023 606/250 |
| 2004/0267260 A1 * | 12/2004 | Mack | A61B 17/7028 606/259 |
| 2005/0065516 A1 * | 3/2005 | Jahng | A61B 17/3421 606/254 |
| 2005/0090898 A1 | 4/2005 | Berry | |
| 2005/0203513 A1 * | 9/2005 | Jahng | A61B 17/1757 606/254 |
| 2005/0203514 A1 * | 9/2005 | Jahng | A61B 17/1757 606/263 |
| 2005/0203517 A1 | 9/2005 | Jahng et al. | |
| 2005/0209694 A1 | 9/2005 | Loeb | |
| 2005/0209697 A1 * | 9/2005 | Paponneau | A61F 2/44 623/17.15 |
| 2005/0261686 A1 * | 11/2005 | Paul | A61B 17/7029 606/254 |
| 2005/0267581 A1 | 12/2005 | Marnay | |
| 2006/0041259 A1 * | 2/2006 | Paul | A61B 17/7023 606/250 |
| 2006/0212033 A1 * | 9/2006 | Rothman | A61B 17/7028 606/328 |
| 2006/0293755 A1 * | 12/2006 | Lindner | A61F 2/442 623/17.15 |
| 2007/0015190 A1 | 1/2007 | Lai | |
| 2007/0016204 A1 * | 1/2007 | Martinez | A61B 17/7059 606/279 |
| 2008/0221620 A1 * | 9/2008 | Krause | A61B 17/7028 606/255 |
| 2008/0312694 A1 * | 12/2008 | Peterman | A61B 17/7028 606/257 |
| 2009/0182378 A1 * | 7/2009 | Choi | A61B 17/7026 606/254 |
| 2009/0270921 A1 * | 10/2009 | Krause | A61B 17/7026 606/254 |
| 2011/0144703 A1 * | 6/2011 | Krause | A61B 17/8625 606/309 |
| 2012/0089188 A1 * | 4/2012 | Jackson | A61B 17/7008 606/254 |
| 2014/0114312 A1 * | 4/2014 | Krause | A61B 17/8625 606/62 |
| 2016/0051287 A1 * | 2/2016 | Krause | A61F 2/44 606/255 |

* cited by examiner

FLEXIBLE SPINE COMPONENTS

BACKGROUND OF THE INVENTION

Field of the Invention

This invention relates to spinal implants to improved flexible elements for the incorporation in spinal implants. Specifically the invention relates generally to flexible rod connectors for dynamically stabilizing a portion of the spine stabilizing two or more bone segments, or use as a vertebral body replacement implant for the replacement of one or multiple spinal vertebra which can possess, at least in one direction, the stiffness properties of the vertebra/disc combination.

Brief Description of the Prior Art

Flexible Fixation Device

The use of fixation devices for the treatment of vertebrae deformities and injuries is well known in the art. Various fixation devices are used in medical treatment to correct curvatures and deformities, treat trauma and remedy various abnormal spinal conditions. Spinal fusion is the standard method of treatment for conditions including spondylolysis, spinal stenosis and other disc disorders. Since fusions have been expanded to treat more conditions and the number of procedures is rising each year, it is apparent that many surgeons believe the procedure is the best possible treatment for their patients. Over the past decades, a variety of spinal implant devices have been used in conjunction with fusion. These include rigid systems such as bone plates, intravertebral cages, rods and hooks, and pedicle screws. Research shows that, when used properly, pedicle screws are the most reliable spinal implant, providing stabilization even in the event of pseudoarthrodesis. This posterior stabilization system involves variable-angle screws inserted into the pedicle of the vertebrae. Fluoroscopic pedicle screws can be detected by radiographic and fluoroscopic imaging during placement, improving the success rate of surgery. These rigid implants can be inserted from an anterior or a posterior approach, although the majority uses the posterior technique. U.S. Pat. No. 6,645,207 to Dixon teaches a posterior system comprised of bone plates, clamps and pedicle screws that allow axial stress in order to improve the fusion procedure by placing it under pressure. Compression at the graft interface is crucial to establishing blood supply and nutrients to the graft. The '207 patent demonstrates that physiological loads and stresses are important to achieve proper healing or adjustment of a damaged vertebrae. Similar patents in this field include U.S. Pat. No. 5,437,669 to Yuan, U.S. Pat. No. 5,474,555 to Puno, and U.S. Pat. No. 6,468,276 to McKay.

There are severe limitations of the fusion procedure including unnatural stresses on the vertebrae adjacent to the fusion, extreme limitation of flexional and torsional movements, and frequent in vivo failure of rigid constructs. Problems with spinal fusions stimulated research of dynamic stabilization devices. Dynamic stabilization is an alternative to vertebral body fusion that stabilizes the damaged spine while permitting motion. The instruments used in dynamic fixation emanate from devices used in conjunction with fusion and are embodied in many different inventions. Pedicle screws are used with the majority of these "soft" stabilization methods, and provide physiologic support and controlled motion by attaching to elastic ligaments or metal rods. Soft stabilization devices are designed to restore the biomechanics of a functional spinal segment. Although the soft stabilizing devices relieve many problems caused by fusion, they also increase the chance of implant failure or improper insertion.

Allowing certain degrees of physiologic motion while maintaining proper rigidity to enhance healing is the most difficult aspect of the design process in the field of dynamic spinal stabilization. The Graf ligament is one of the earliest nonfusion techniques, consisting of elastic bands looped around pedicle screws. U.S. Pat. No. 5,092,866 to Breard and Graf describes this system of non-metallic loops, secured to either the spinous processes or pedicle screws, which permit the patient certain degrees of flexional and torsional movements. The semi-elastic ligament keeps sufficient space between the vertebrae which encourages proper healing. This idea has been sophisticated by subsequent researchers who have produced new methods to neutralize unstable vertebrae and the following are some typical inventions in this field. U.S. Pat. No. 6,966,910 to Ritland describes two pedicle screws anchoring a metallic rod component with several embodiments, including multiple geometries and dual rods. In the '910 device, the geometry of the metal rods produce the flexible or semi-elastic stabilization. U.S. Pat. No. 5,282,863 to Burton teaches a system that achieves dynamic fixation of the spinal column by using a non-metallic, porous material as the rod component, rather than conventional metallic rods, to increase flexibility of the implant. U.S. Pat. No. 7,083,621 to Shaolian that utilizes ball-and-socket connections between rods and bone screws that dynamically stabilize the damaged spine. The specialized rods described in the '621 patent can be inserted into the portals of the bone anchors and allow for angular articulation of the device. U.S. Pat. No. 7,018,379 to Drewry teaches a system of bone screws and fasteners that attach a flexible elongated member which is tensioned to provide corrective forces to the spine. Another motion-preserving device presented in U.S. Pat. No. 6,989,011 to Paul incorporates at least one tube with helical slits down the length. This dynamic rod or rods act to support a vertebral motion segment and allow controlled degrees of movement. The angular range of the '011 rod can be modified by altering the pitch and direction of the slits. U.S. Pat. No. 6,293,949 to Justis uses a longitudinal member at least partially composed of a pseudo-elastic shape-memory material that is anchored by bone screws. The longitudinal member reforms to a new configuration under stress then returns to the initial configuration when the stress is removed, providing flexible support for the cervical spine Problems with spinal fusions stimulated research of dynamic stabilization devices. Pedicle screws are used with the majority of these "soft" stabilization methods, and provide physiologic support and controlled motion by attaching to elastic ligaments or metal rods. Dynamic stabilization devices are designed to restore the biomechanics of a functional spinal segment. Although the dynamic stabilizing devices relieve many problems caused by fusion, they also increase the chance of device failure or improper insertion.

Subsequent researchers who have produced new methods to neutralize unstable vertebrae have sophisticated this idea introduced by Gaf. A flexible posterior stabilization system, DYNESYS (dynamic neutralization system) developed in 1994 and now marketed by Zimmer (Warsaw, Ind.), is now gaining popularity among orthopedic surgeons in the US as an alternative to fusion. Anchored by pedicle screws, Dynesys uses preloaded stabilizing cords and spacers to provide uniform system rigidity. Fusion is an outdated and inelegant technique that permanently eliminates normal biomechanical motion of the spine. The dynamic stabilization systems are important alternatives to fusion and are the future for the treatment of vertebral instability.

A need has thus arisen for improvements in dynamic stabilization instruments, and the present invention offers that advancement through the development of the flexible connecting rod for posterior implantation on damaged vertebrae.

In another application when a vertebra is broken, crushed or diseased, it is frequently necessary to ablate the body of the crushed or diseased vertebra. In order, however to prevent the spinal column from collapsing with damage to the spinal cord running in the vertebral foramen forward of the vertebral body, it is necessary to employ a spacer. This device is braced vertically between the bodies of the adjacent vertebrae and holds them apart at the desired spacing. A substitute vertebra with biofidelic properties would provide the optimum replacement Various implants have been developed to address structural failure of various parts of the spinal column. The prior art with respect to spinal column implants falls into two general categories: intervertebral disc prostheses, and rigid vertebral body prostheses.

Vertebral body prostheses have been disclosed in US Patents such as U.S. Pat. Nos. 3,426,364, 4,401,112, 4,554,914, 4,599,086, 4,932,975, and 5,571,192. The referenced patents typically are composed of a rigid, height adjustable device typically a threaded cylinder or turnbuckle mechanism with anchoring plates. Another type of replacement device is composed of individual elements that are sized and adapted to be fitted together to provide support to the adjacent vertebra. This type of device has been described in U.S. Pat. Nos. 5,147,404 and 5,192,327.

The devices presented in those patents are intended for situations where it is necessary to remove a vertebral body. That, in turn, requires the resection of adjacent intervertebral discs. A problem common to all of such prior devices is that they adequately provide the structure of the removed vertebral body but fail to provide the flexibility of the removed intervertebral discs.

Accordingly it is an object of this invention to provide a flexible components that will flex, bend or curve to allow or duplicate the natural movement of the spinal segments.

These and other objects, features, advantages and aspects of the present invention will be better understood with reference to the following detailed description of the preferred embodiments when read in conjunction with the appended drawing figures.

SUMMARY OF THE INVENTION

The present invention overcomes the deficiencies and problems evident in the prior art as described herein above by combining the following features into an integral, longitudinally, laterally and torsionally flexible component.

A slot of substantial length and width extends in a generally helical path, either continuously or intermittently, around and along the tubular member. The slot follows a serpentine or predetermined path along the helical path generally around and along the tubular member. Advantageously, the slot is cut at an angle normal to the shaft using a computer controlled cutting technique such as laser cutting, water jet cutting, milling or other means. Additionally, this slot may be cut at an angle to the normal so as to provide an undercut slot; preferably the angle is in the range from about 10 to about 45 degrees from the normal.

A plurality of slots can be employed thereby increasing the flexibility of the component, relative to a shaft having a single slot of identical pattern. The serpentine path forms a plurality of teeth and complimentary recesses on opposite sides of the slot. The slot has sufficient width to form an unbound joint permitting limited movement in any direction between the teeth and the recesses, thereby providing limited flexibility in all directions upon application of tensile, compressive, and/or torsion forces to said component. In a similar manner the slot can have increased width in one direction compared to another direction thus providing increased flexibility in one direction.

The flexible component can have different degrees of flexibility along the length of said shaft. The varied flexibility can be achieved by having the pitch of the helical slot vary along the length of the shaft. The varied flexibility corresponds to the variation in the pitch of the helical slot. The helical path can have a helix angle in the range of about 10 degrees to about 45 degrees, and the helix angle can be varied along the length of the shaft to produce correspondingly varied flexibility. Alternatively, the width of the helical slot can vary along the length of the shaft to provide the varied flexibility. The rigidity of the flexible shaft can be achieved through the design of the slot pattern, thereby enabling the use of thinner walls than would otherwise be require to produce equivalent rigidity. In a preferred embodiment, the ratio of the amplitude of the serpentine path to the pitch of the slot is in the range from greater than 0.1 to about 0.8.

The slot can be filled with a resilient material, partially or entirely along the path of the slot. The resilient material can be an elastomer compound which can be of sufficient thickness to fill the slot and to encapsulate the entire shaft thus forming an elastomer enclosed member. The elastomer can be a resilient material such as a urethane or a silicone compound. The rigidity of the flexible shaft can be further achieved or varied through the use of filler material having different stiffness properties, thereby enabling the use of thinner walls than would otherwise be require to produce equivalent rigidity.

Preferably, the flexible shaft is formed by laser cutting an elongated tubular member of substantial wall thickness, to form the slot around and along the tubular member in a helical manner. A serpentine path can be superimposed on a helical wave in the form of a generally sinusoidal wave Preferably, the sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

An important aspect of this invention therefore lies in providing a prosthesis for total replacement of a vertebral body and adjacent discs that will provide the flexibility and stiffness of the resected vertebra and, when properly in place, provides a stress environment at the prosthesis/bone interface similar to normal in vivo conditions. Specifically, the invention can be utilized to produce an implant in which the normal ranges of movement are preserved, the prosthesis permitting limited longitudinal flexure, slight compression and expansion, and even a limited degree of torsional movement that at least approximates a normal vertebral response.

It is a further object of this invention to provide a tubular device which will have certain axial, bending and torsional stiffness for a vertebral body replacement implant.

BRIEF DESCRIPTION OF THE DRAWINGS

These and other objects, features, advantages and aspects of the present invention will be better understood with reference to the following detailed description of the preferred embodiments when read in conjunction with the appended drawing figures.

DEFINITIONS AND TERMS

Figure 1:
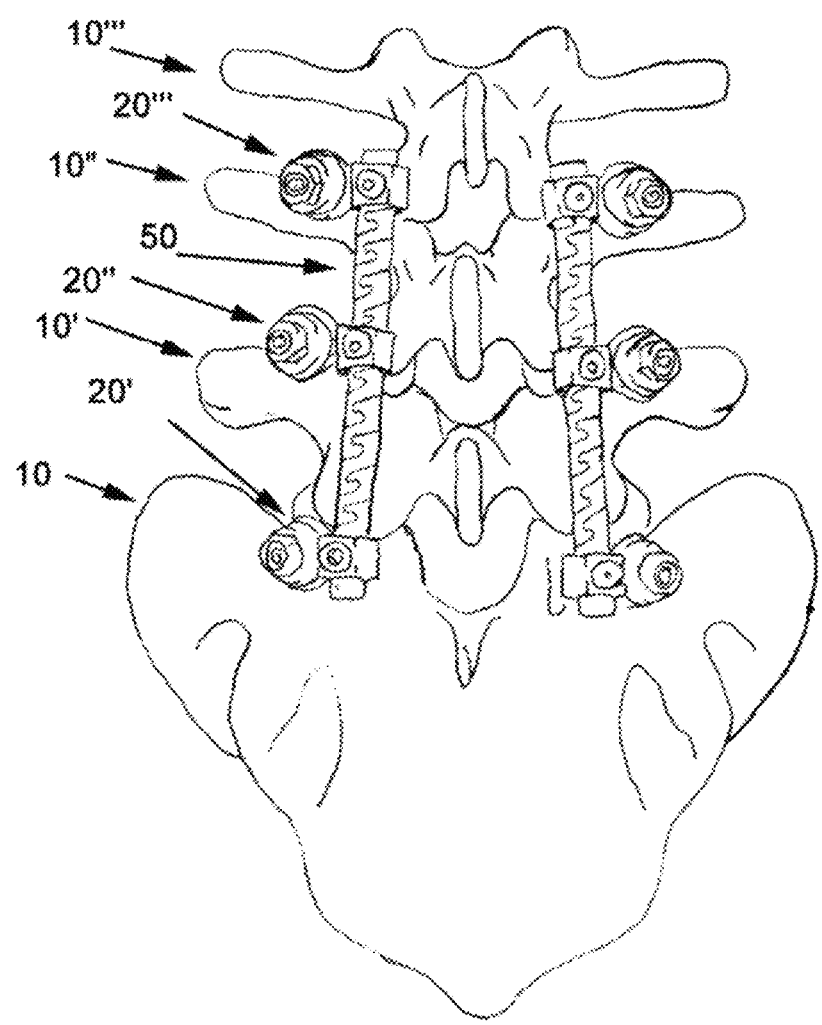
FIG. 1 is a schematic representation of a flexible spinal element attached to the lumbar region of the spine and having the helical slot extending the majority of the length of the element in accordance with the invention.

The term slot as used herein, is defined in the American Heritage Dictionary, 3rd Edition, Copyright 1994, as follows:

For the purposes herein the terms "slit" and "slot" are used interchangeably, consistent with their definitions, as follows:

a. slot n. 1. A narrow opening; a groove or slit: a slot for coins in a vending machine; a mail slot.
  i. 2. A gap between a main and an auxiliary airfoil to provide space for airflow and facilitate the smooth passage of air over the wing.

For the purposes herein the term pitch as used herein is defined as:

i. pitch-n. 1. The distance traveled by a machine screw in one revolution.
ii. 2. The distance between two corresponding points on adjacent screw threads or gear teeth.

For the purposes herein the term helix angle, shall define the angle formed between the plane perpendicular to the longitudinal axis of the shaft and the helical path of the spiral along the shaft. The term helix angle can also be defined mathematically as the arc tangent of the pitch of the helix divided by the circumference of the shaft.

For the purposes herein the term "cycle" shall refer to:

i. Cycle-1. An interval of time during which a characteristic, often regularly repeated event or sequence of events occurs: Sunspots increase and decrease in intensity in an 11-year cycle.
ii. 2.a. A single complete execution of a periodically repeated phenomenon: A year constitutes a cycle of the seasons.
iii. 2b. A periodically repeated sequence of events: cycle includes two halves of the sine-wave like undulation of the slot path.

For the purposes herein the term "spiral" shall refer to:

i. Spiral 1a. A curve on a plane that winds around a fixed center point at a continuously increasing or decreasing distance from the point.
ii. 1b. A three-dimensional curve that turns around an axis at a constant or continuously varying distance while moving parallel to the axis; a helix.
iii. c. Something having the form of such a curve: a spiral of black smoke.
iv. 2. Printing. A spiral binding.
v. 3. Course or flight path of an object rotating on its longitudinal axis.
vi. 4. A continuously accelerating increase or decrease: the wage-price spiral.

b. Spiral (adj.)
  1. Of or resembling a spiral.
  2. Circling around a center at a continuously increasing or decreasing distance.
  3. Coiling around an axis in a constantly changing series of planes; helical.

For the purposes herein the term "amplitude" shall refer to the maximum absolute value of the periodically varying quantity of the slot.

a. The spiral is more explicitly helix-like, in that it is a three-dimensional curve that lies on a cylinder, so that its angle to a plane perpendicular to the axis is constant. However, along the length of the shaft, the helix angle can vary so as to impart changes in flexibility to the overall shaft. Using an electronics analogy, the helix can be viewed as a carrier wave with the slot following the path of the modulation of the carrier wave. The teeth or interlocking regions of the cycle, form a ratchet-like structure, in that one set of teeth engage the other set of sloping teeth, permitting motion in one direction only.

b. For the purposes herein the term "frequency" shall refer to the number of times a specified phenomenon occurs within a specified interval:

i. Frequency.
ii. 1a. Number of repetitions of a complete sequence of values of a periodic function per unit variation of an independent variable.
iii. 1b. Number of complete cycles of a periodic process occurring per unit time.
iv. 1c. Number of repetitions per unit time of a complete waveform, as of an electric current. The number of times the cycles form a repetitive pattern in one unit of length is the frequency of the slot pattern. The number of cycles "C" of the slot undulations superimposed upon the helical path which are present in one revolution around the shaft, is referred to as the cycles per revolution.

For the purposes herein the coined term "Biofidelic" shall refer to the mechanical structures that attempt to duplicates biological structures with a high accuracy of fidelity.

For the purposes herein the term "spinal element" shall refer to a solid rod or tube manufactured of a biocompatible material that can receive a slot or cut to provide flexibility.

DETAILED DESCRIPTION OF THE PREFERRED EMBODIMENTS

While the present invention will be described more fully hereinafter with reference to the accompanying drawings, in which particular embodiments and methods of implantation are shown, it is to be understood at the outset that persons skilled in the art can modify the invention herein described while achieving the functions and results of this invention. Accordingly, the descriptions that follow are to be understood as illustrative and exemplary of specific structures, aspects and features within the broad scope of the present invention and not as limiting of such broad scope.

The present invention is directed to dynamic stabilization systems for use with the anterior, antero-lateral, lateral, and/or posterior portions of at least one motion segment unit of the spine. The systems of the invention are designed to be conformable to the spinal anatomy and provide controlled, dynamic stabilization.

The system of the invention can be used on the cervical, thoracic, lumbar, and sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with the disclosed spine stabilization system restores a more natural movement and provides added support to the strain-susceptible area.

One embodiment of the spine stabilization system of the present invention includes bone fasteners, for example pedicle screws, the disclosed end plates or hooks, and at least one flexible spinal element with or without additional connecting rods. The flexible element advantageously provides desirable properties for bending or twisting that allows the system to accommodate the natural spine movement. The flexible element preferably approximates or resembles a relatively circular metallic or polymeric tube or rod with an appropriately formed slot that extends spirally around the shaft either continuously or segmentally, the basic concept of which is described by Krause et al (U.S. Pat. Nos. 6,053,922 and 6,447,518). In another embodiment, the spinal element and flexible segments of the element can be combined with a polymeric material as described hereinafter.

In some embodiments the central portion of the flexible element is hollow, resembling a hollow tube. A skilled artisan would appreciate that there are several ways to form a hollow tube, regardless of whether it is circular or any other cross-sectional shape. For example, extruding a material, such as metal or polymeric materials, through a die, can form the tube. One or more of the patterns described hereinafter can then be cut into the extruded material. For instance, a tube can have a helical spiral slit or serpentine cut along at least a portion of the tube or the tube can have a plurality of diagonal slits cut into its surface, by using a laser or by other suitable methods.

The following examples describe embodiments using a solid rod or tube. It should be understood that in these examples the flexible elements described herein can be replaced with flexible elements having different shapes or configurations, including, but not limited to, the many variations described herein.

The disclosed system has several closely related embodiments, all using the flexible spinal element. The selection of a specific embodiment for a particular application will be obvious to one skilled in the medical arts upon reading the teachings herein.

Figure 2A:
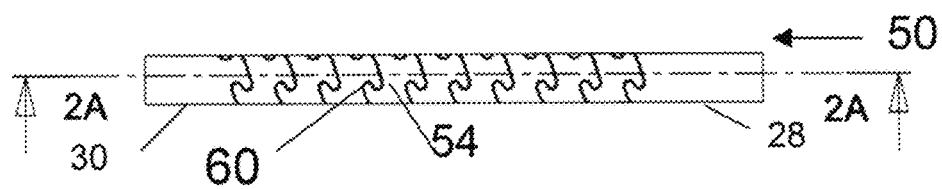
FIG. 2A is a schematic representation of the flexible spinal rod of FIG. 1, showing general pattern of the helical serpentine slot along the length of the rod in accordance with the invention.
Figure 2B:
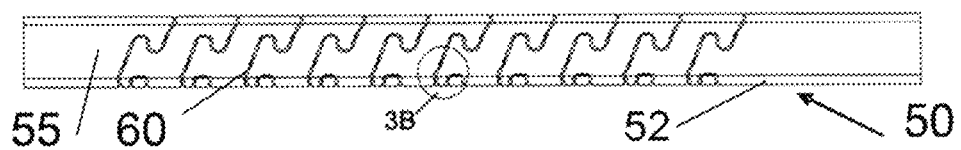
FIG. 2B is a cross sectional view of the flexible spinal rod though the longitudinal axis of FIG. 2A, showing general pattern of the helical serpentine slot along the length of the rod in accordance with the invention.

The invention relates to a flexible spine stabilization system having one or more flexible segments within a spinal element. The flexibility is created through the use of at least one helically slit formed in the spinal element. Additional flexible segments also have at least one helical slit in either the same helical rotation and pattern or in an opposite rotation and/or different pattern. One or more fasteners are connected to or in communication with the distal and proximal attached ends of the spinal elements as known in the medical arts. In another embodiment the flexible spine stabilization system has a flexible segment that has at least one helical, serpentine slot within a section of the spinal element that is embedded within a polymer or other flexible material so as to fill the slot with the flexible material. In an additional embodiment the flexible spine stabilization system uses a hollow flexible element that encompasses a polymer or other flexible material within its central core without extending into the helical slot(s). A further embodiment uses a flexible slotted segment within the spinal element that contains a polymer or other flexible material within the central core with the flexible material extending radially outward through the helical, serpentine slot(s). The flexible spine stabilization system can further incorporate a flexible slotted segment that contains a polymer or other flexible material within the central core of the spinal element and/or flexible segment that extends radially outward through the slot and encompasses the outer surface of the spinal element and/or the flexible segment. The dynamic stabilization system of the present invention generally consists of a spinal element 50 and pedicle screws 20, as illustrated in FIGS. 1, 2A and 2B, which are connected to two or more vertebra 10, 10', 10" and 10'" spanning the area fused or damaged area. The spinal element 50 in this embodiment generally consists of a hollow tube having an outer surface 54 and a hollow central core 55 as illustrated hereinafter. A slot 60 is cut through the wall 52 of the spinal element 50 to form a serpentine, helical path that extends generally along the path of a spiral around the entire length of the spinal element 50. The extension of the helical slot continually over most of the length of the spinal element 50 enables the majority of the element 50 to flex. Although pedicle screws 20 are illustrated herein as being attached to the proximal attachment end 28 distal attachment end 30, as well as the central portion of the spinal element 50, hooks or other known attachment members can be substituted as known in the art. It should be noted that the pedicle screws can be affixed to slotted portions of the spinal element as non-slotted portions.

Figure 3:
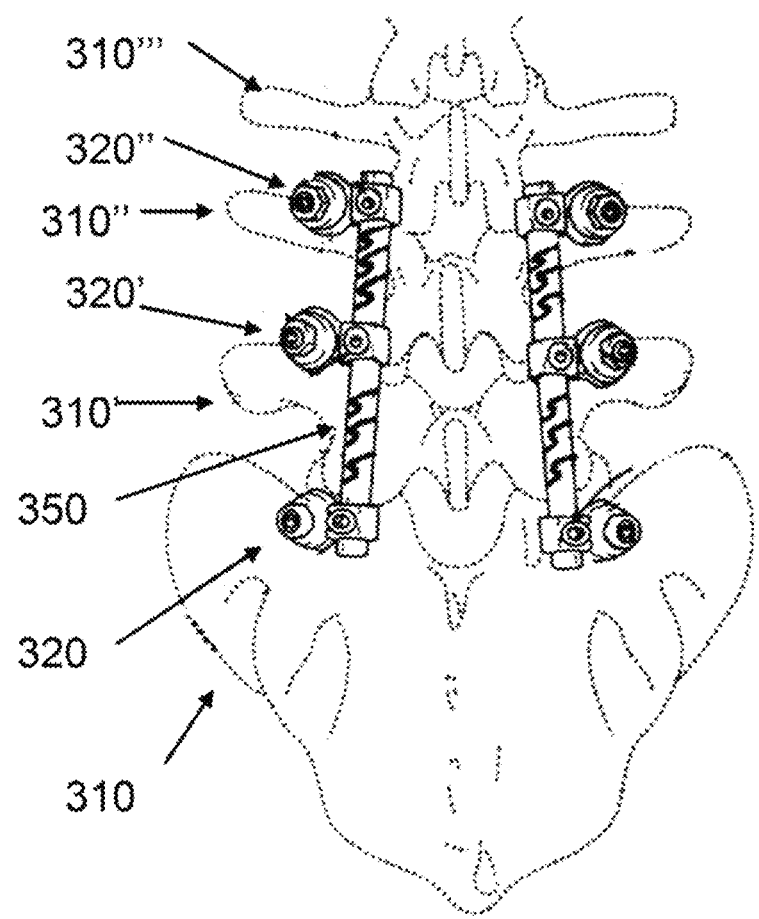
FIG. 3 is a schematic representation of a flexible spinal element attached to the lumbar region of the spine and having the helical slot extending only between the attachment members in accordance with the invention.
Figure 4:
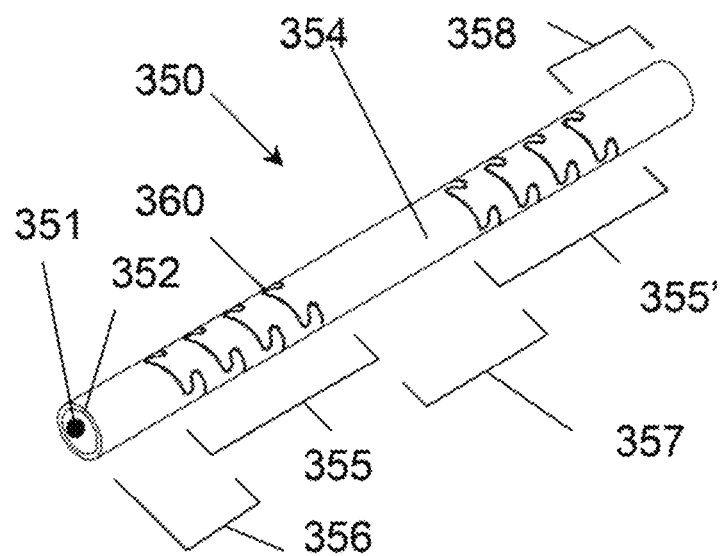
FIG. 4 is perspective view of spinal element of FIG. 3.

In FIGS. 3 and 4, the dynamic stabilization system of the present invention generally consists of a spinal element 350 and pedicle screws 320 which are connected to two or more vertebra 310, 310', 310" and 310'" spanning the fused or damaged area. As with the embodiment of FIG. 1, the spinal element 350 of FIG. 3 generally consists of a hollow tube having an outer surface 354 and a hollow central core 351 as illustrated in FIG. 4. A slot 360 is cut through the wall 352 of section of the spinal element 350 to form a flexible segment 355 having a serpentine, helical path. In this embodiment the helical slot 360 allows for flexibility only within the flexible segments 355 and 355'. The sections of the spinal element 350 that are not slotted remain relatively rigid and are used for attachment with the pedicle screws 320 at the proximal attachment end 356 distal attachment end 358 and/or central section 357. Although FIGS. 3 and 4 illustrate two flexible sections 355 and 355', the number would be dictated by the number of vertebral discs requiring flexible support and would be obvious to those skilled in the art.

Figure 5:
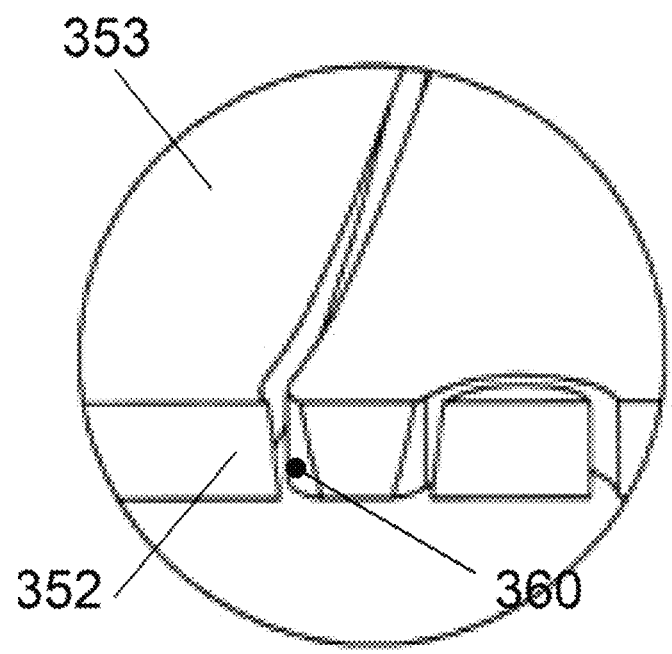
FIG. 5 is a magnified view of the unfilled slot as used in the disclosed spinal elements in accordance with the invention.

A magnified view of a slot is illustrated in FIG. 5. The slot 360 is representative of all the slots disclosed herein in that way that it is cut through the wall 352 into the core 351. Although the slots disclosed herein are of different patterns, this is purely a function of flexibility and all have the same basic construction. The criticality to the disclosed invention lies in the ratios and dimensions rather than the process of placing a rod or tube. In the following description of the criteria of the slots, no reference numbers specific to other figures are used, as the criteria are applicable to all slot configurations. Although the general concept of the spiral slot is disclosed in the above referenced patents, the shaft as taught in '922 and '518 cannot be use in the spinal application. The shaft taught in '922 and '518 is generally used for the transmission of rotary power for use in reaming a curved structure and must therefore have different critical criteria than the disclosed rod. The '922 and '518 flexible shaft must also have an attachment to a power source and an attachment for a tool.

The helical path of the slot is about 1 to about 6 cycles per diameter length. In order to provide the desired flexibility, while maintaining support, the width of the slot should not exceed about 0.15 of an inch in a rod having a diameter in the range from about 0.10 to about 1.5 inches, with a general width of about 0.005 to about 0.15 inches. Or alternatively stated, the slot width is between about 2.5% and about 20% of the diameter of the spinal element. This is in contrast to the slot width of the '922 and '518 patents that ranges from 0.01-0.5. The helical angle differs also in that in the pending application the angle ranges from about 5 degrees to about 20 degrees while in the '922 and '518 patents the helical angle ranges between 10 degrees and 45 degrees.

Figure 6:
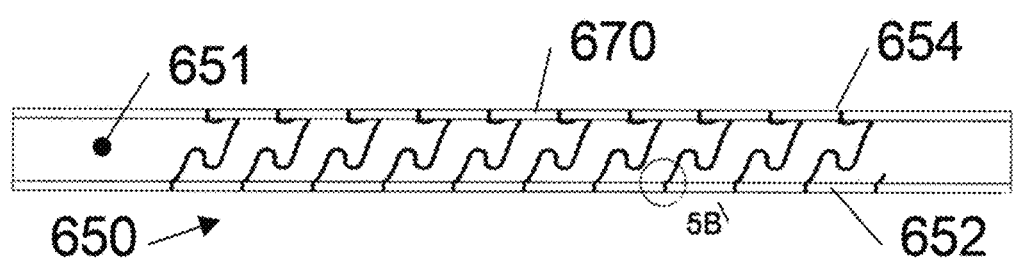
FIG. 6 is a sectional illustration though the longitudinal axis of the spinal element showing the slot with a resilient filler in a portion of the slot in accordance with the invention.
Figure 7:
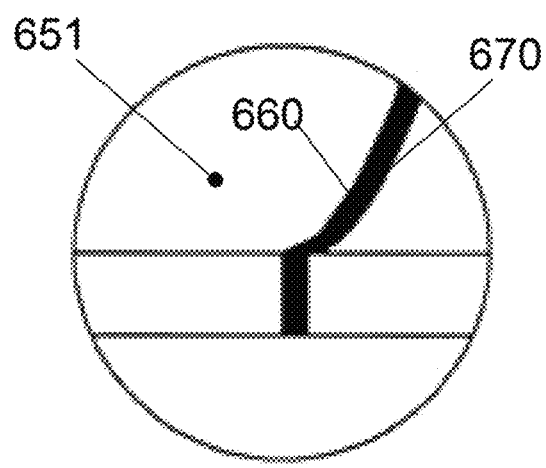
FIG. 7 is a magnified view of the area 58B in FIG. 6 in accordance with the invention.

In the embodiment illustrated in FIGS. 6 and 7, a resilient flexible or elastomeric material 670 fills only the slot 660 of the spinal element 650. The exterior surface 654 of the spinal element 650 remains uncovered by the material 670, as does the interior surface 653. The addition of the elastomeric material 670 to the slot 660 provides resistance to the flexibility of the spinal element 650 as well as preventing tissue and scar ingrowth into the slot.

Figure 8:
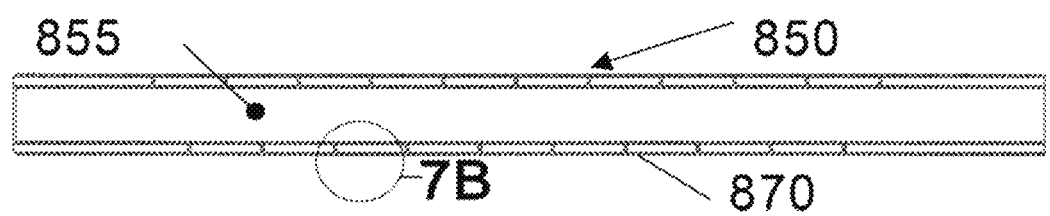
FIG. 8 is a sectional illustration though the longitudinal axis of the spinal element showing the filled slot with a resilient filler encapsulating the entire tube.
Figure 9:
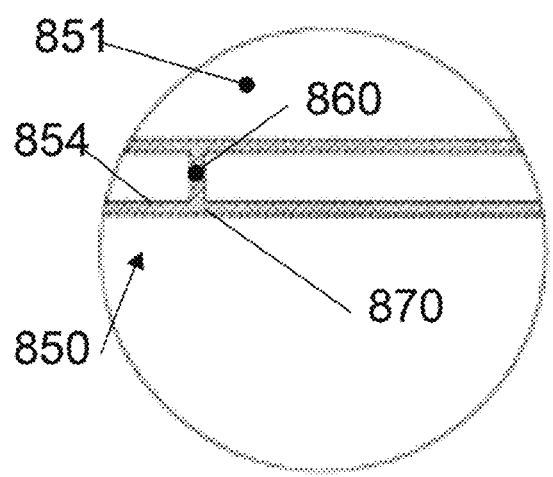
FIG. 9 is a magnified view of the area 7B in FIG. 8 in accordance with the invention.

In FIGS. 8 and 9 the spinal element 850 the elastomeric material 870 encapsulates the spinal rod 850 as well as filling the slots 860. In this embodiment, the interior and exterior surfaces, but not filling the core 855, of the spinal element 850 is covered by the elastomeric material 870 to prevent tissue ingrowth into the slot and increase the stiffness of the spinal element. Although in these figures the elastomeric material 870 also fills the slots 860, it should be noted that the elastomeric material 870 can only encapsulate the spinal element 850 without filling the slots 860. Additionally, just the interior or exterior of the spinal element can be covered with the elastomeric material with the slots being either filled or unfilled. As noted above, the addition of the elastomeric material 870 increases the resistance to flexing and is not reflective of the advantages of encapsulating the spinal element 850 with the elastomeric material 870.

Figure 10:
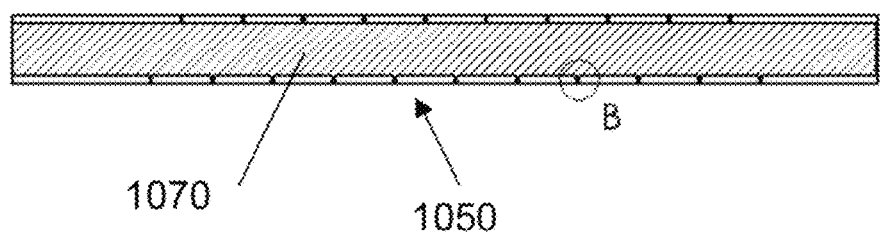
FIG. 10 is a sectional illustration though the longitudinal axis of the spinal element showing the resilient filler occupying the central core and filling the slot in accordance with the invention.
Figure 11:
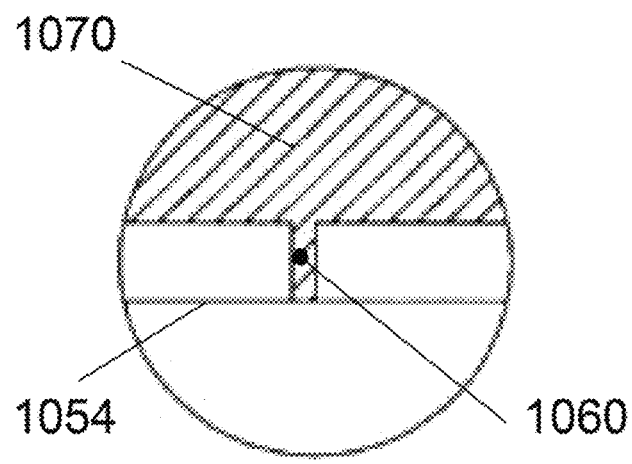
FIG. 11 is a magnified view of the area B of FIG. 10 in accordance with the invention.

In FIGS. 10 and 11 the elastomeric material 1070 completely, or partially, fills the central core 1055 and the slot 1060. The elastomeric material 1070 can fill the central core 1055 only adjacent to the slot 1060 or slots, or the entire central core 1055. By filling the central core 1055, flexibility is further decreased. By adjusting the amount of the central core 1055 that is filled, the flexibility can be adjusted.

Figure 12:
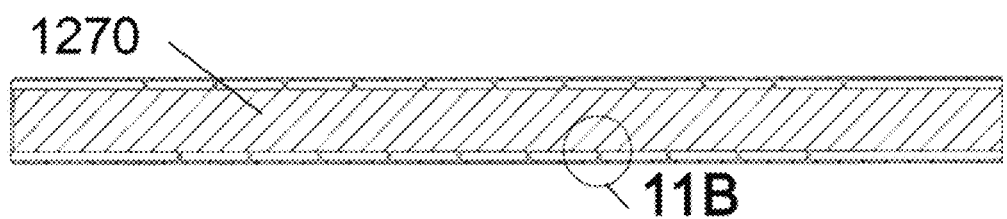
FIG. 12 is a sectional illustration though the longitudinal axis of the spinal element showing the resilient filler occupying the central core and encapsulating the entire tube in accordance with the invention.
Figure 13:
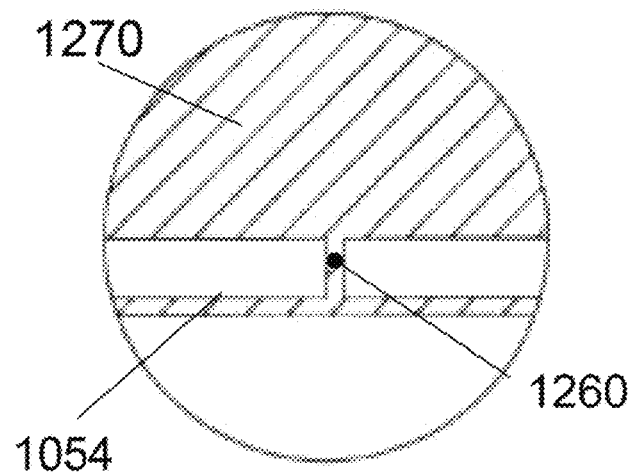
FIG. 13 is a magnified view of the area 11B of FIG. 12 in accordance with the invention.
Figure 14A:
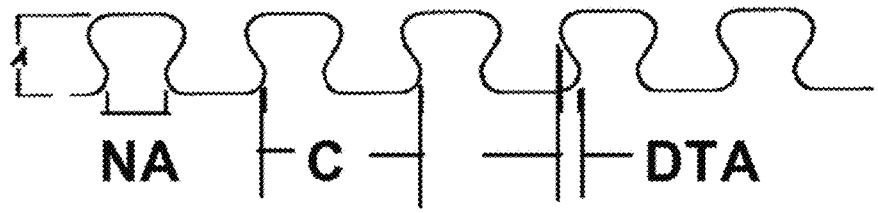
FIG. 14a-14k show schematic representations of additional spiral slit patterns in accordance with the invention.
Figure 14B:
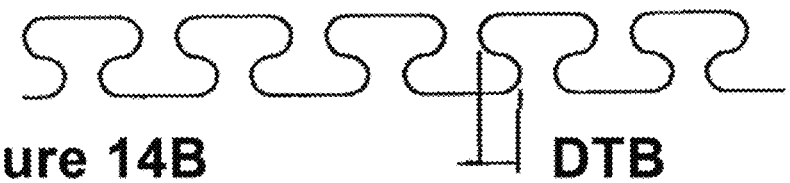
Figure 14C:
Figure 14D:
Figure 14E:
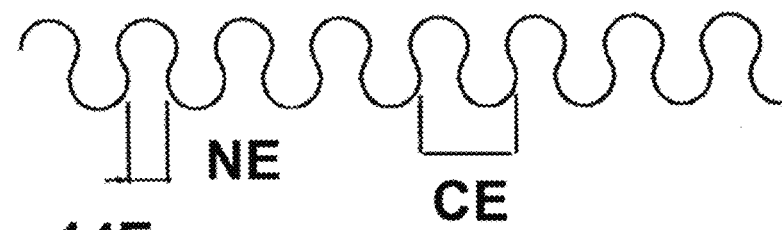
Figure 14F:
Figure 14G:
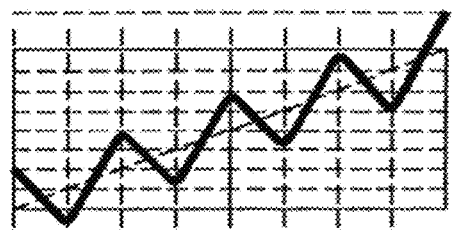
Figure 14H:
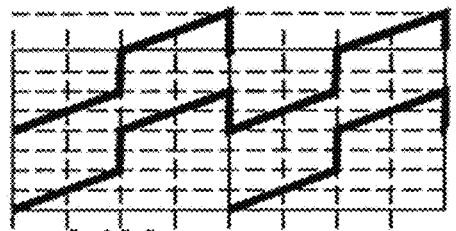
Figure 14I:
Figure 14J:
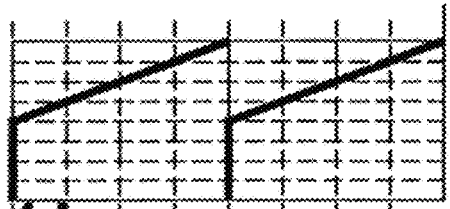
Figure 14K:
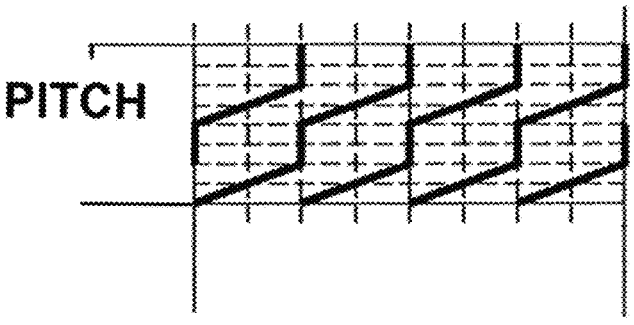

In FIGS. 12 and 13, the elastomeric material 1270 fills the central core 1255, slot 1260 and covers the outer surface 1254. As stated with reference to FIGS. 10 and 11, the elastomeric material 1270 can either fill the central core 1255 adjacent to the slot 1260 or the entire length. This embodiment provides the greatest resistance to flexing when using the hollow tube.

It should be noted that the elastomeric material used herein can also be varied in its material properties, thereby further controlling the amount of flexibility.

A variety of slot patterns are illustrated in FIG. 14 A-K. The patterns are representative of patterns that can be used and are not intended to be all inclusive. As illustrated in FIG. 14A, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 14A and DTB for FIG. 14B. The pattern of 14C, does not provide dovetailing, and requires a helix angle that is relatively small. The pattern of FIG. 14G is an interrupted spiral in which the slot follows the helical path, deviates from the original angle for a given distance, and then resumes the original or another helix angle. Additional patterns, as shown in FIGS. 14D, 14E, 14F, 14H through 14K can have a configuration as illustrated in U.S. Pat. No. 6,447,518, the disclosure of which is incorporated herein by reference, as though recited in detail.

Figure 15A:
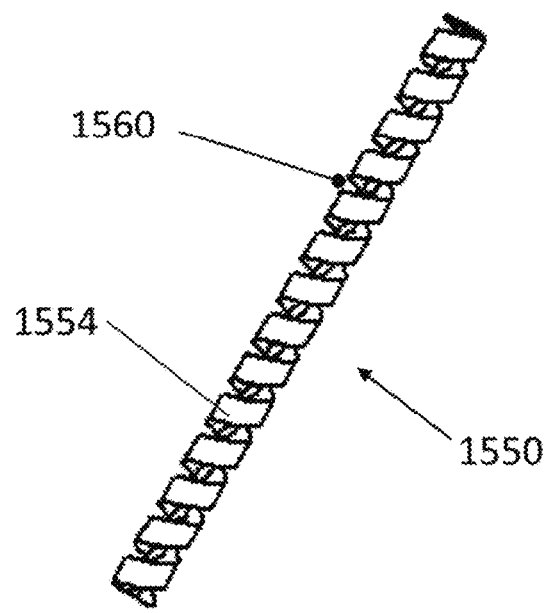
FIG. 15A is a schematic representation of the flexible spinal element, showing a general pattern of the helical slot along the length of the spinal element in accordance with the invention.
Figure 15B:
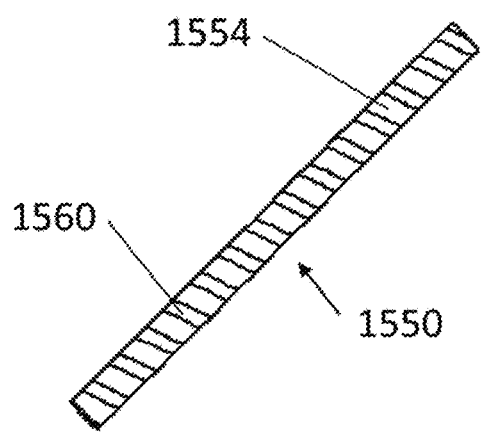
FIG. 15B is a schematic representation of the flexible spinal element, showing a general pattern of the helical slot with the elastomeric filler within the slot along the length of the spinal element in accordance with the invention.
Figure 16:
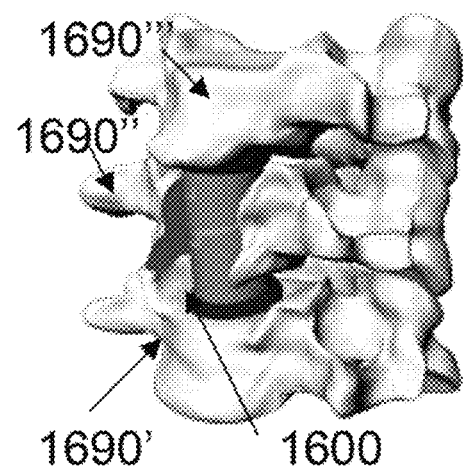
FIG. 16 is schematic representation of one embodiment of the spinal element as a vertebral replacement inserted between vertebra of the spine in accordance with the invention.
Figure 17:
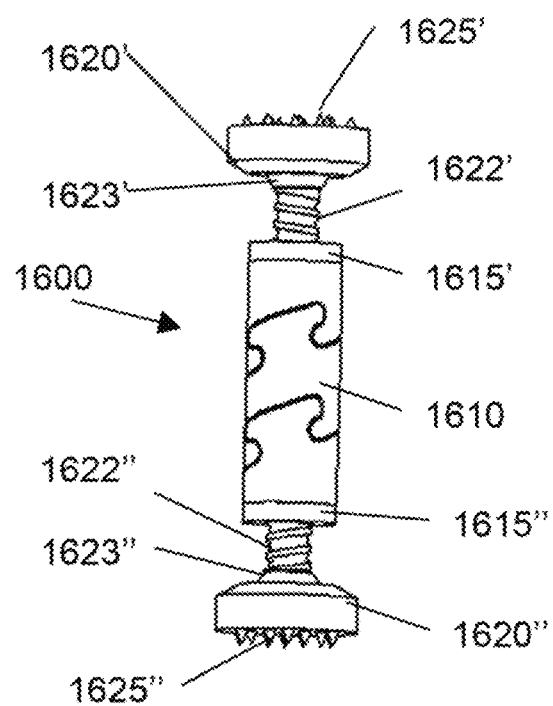
FIG. 17 is plan view of the disclosed spinal element used as a vertebral body replacement consisting of adjustable height end caps for securing the device to the adjacent vertebra in accordance with the invention.
Figure 18:
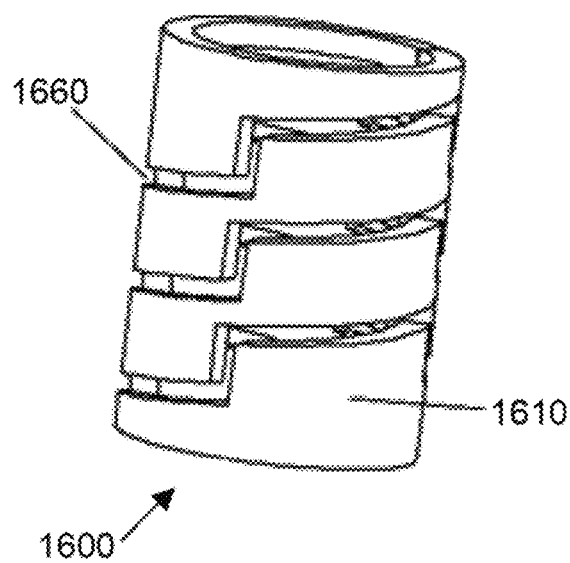
FIG. 18 is a perspective of the central core of FIG. 16 prior to encapsulation with an elastomeric resilient filler material in accordance with the invention.
Figure 19:
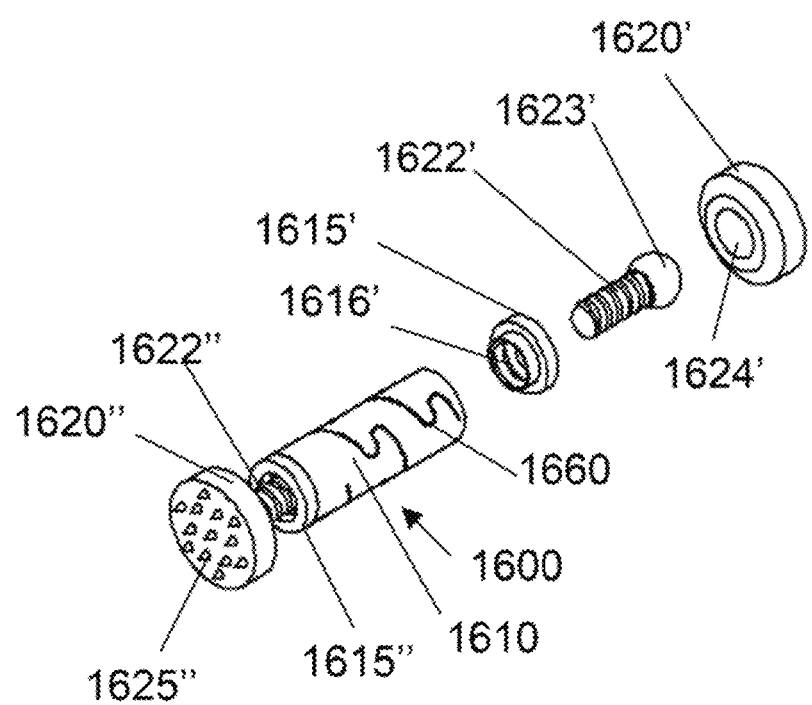
FIG. 19 is an exploded perspective view of the spinal element of FIG. 17.

FIGS. 15A and 15B illustrate the spinal element 1550 with a non-serpentine helical cut. The straight helical slot is 1560 cut into the surface 1554, in the illustrated figures, into a solid rod, although as taught herein the spinal element can also be a tube. As also taught, the slot 1560 can be filled with an elastomeric material 1570 to alter the stiffness properties of the spinal element. Although the entire spinal element 1550 is illustrated herein as having a slot 1560, any of the disclosed embodiments showing only portions of the spinal element 1550 cut can incorporate the non-serpentine helical cut. It should be noted that any of the combinations of elastomeric material and slots can be also incorporated with a solid rod with the obvious exceptions of filling the interior.

Figure 20:
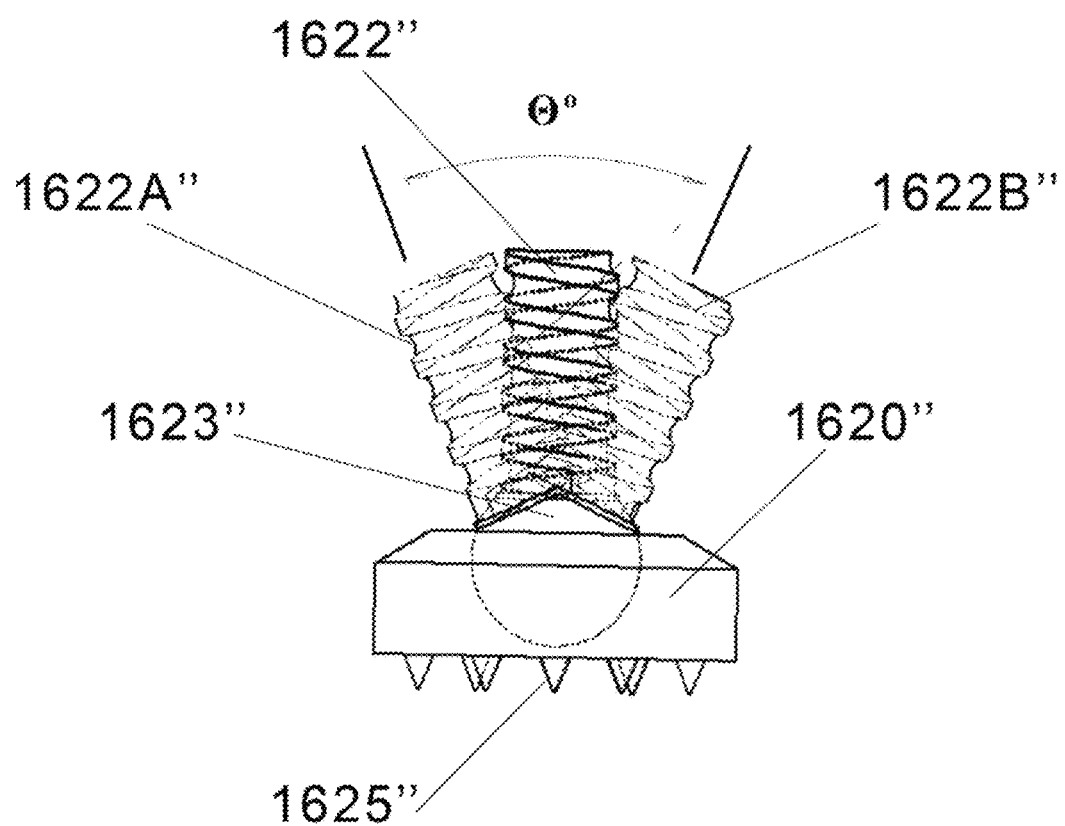
FIG. 20 is a schematic of the end cap used to attach into the central core and fixate to the vertebral body in accordance with the invention.

In another embodiment of the invention illustrated in FIGS. 16-20, the spinal element is used as a central section of a vertebral body replacement implant 1600 formed of rigid biocompatible material such as, for example, stainless steel or titanium, for use in the cavity left after removal of a diseased or defective vertebra 1690" in a human or animal spine. The vertebral body replacement 1600 is situated spanning the diseased vertebra 1690" and attached to the adjacent vertebra 1690' and 1690"'. The spinal element 1610 is connected with an upper endplate 1620' and lower endplate 1620" by means of a threaded rods 1622' and 1622" respectively. The threaded rod 1622' is movably secured to end cap 1615' through internal treads 1616' in the endcap 1615 to allow for height adjustment. Preferably one endplate 1620' has right handed thread and the opposite endplate 1620" has a left handed thread such that rotating the spinal element 1610 will cause an increase in the overall distance between the endplates 1620' and 1620' from the spinal element 1610 and rotation in the opposite direction will reduce the overall distance. The balls 1623' and 1623" at the ends of the threaded rods 1622' 1622" are attached to the endplates 1622' 1622" through sockets 1624' and 1624" or similar rotational allowance coupling to allow for angular alignment to the vertebra, one end of which is illustrated in FIG. 20. Attachment to the upper endplate 1620' and the lower endplate 1620" to the adjacent vertebra 1510' and 1510" is through spikes 1625', 1625" or other means known in the medical arts. The spinal element 1610, FIGS. 17 and 18, has a spiral, helical slot 1660 machined in the body. The slot 1660 configuration and properties of the cylindrical body and optional elastomeric filler are designed to duplicate the stiffness, within a reasonable allowance, of the vertebra and adjacent intervertebral disc of human specimens. The spiral slot 1660 cut into the spinal element 1610 can have an elastomer (not shown) or otherwise flexible material interposed within the slot 1660 and/or the central core of the spinal element, as describe previously, to further enhance the flexibility of the shaft and to alter the torsional response or bending stiffness of the member. The elastomer can be used as a shock absorbing or cushioning member. To facilitate manufacture, and to provide protection of the tubular member, the elastomer can encapsulate the entire shaft or coupler, thus forming a tubular construction. Alternatively, the interior of the spinal element 1610 can be threaded fully or partially and the threaded rods 1622' 1622" affixed directly to the spinal element 1610 thereby eliminating the endcaps 1615' 1615".

The upper and lower endplates 1620' 1620" are configured to provide anchoring with the adjacent vertebra by means of spikes 1625', 1625", screws or other means. The end plates can contain holes through which the screws or pins can be passed into the adjacent vertebra. The screws or fixation pins would pass through the implant endplate and/or alignment disc to rigidly fix the implant to the adjacent vertebra and allow for the natural curvature of the spine. It the thickness of the alignment discs will preferably be supplied in various thicknesses to compensate for the height of the removed vertebra and discs.

The method of implantation of the spinal element as configured as a vertebral body replacement implant 1600 of a diseased or fracture vertebra 1690 to restore the height and functionality of the spinal column is described. The assembled endplates 1620' 1620" and threaded rod 1622' 1622" as shown in FIG. 20 is inserted into the appropriate sized spinal element 1610 with endcaps 1615' 1615" previously attached. The endcaps 1615' 1615" can be affixed to the spinal element 1610 at the time of manufacture or subsequently as known in the medical arts. The endplates 1620' 1620" are positioned for minimum or appropriate height to be inserted in the prepared cavity of the vertebra 1690. The spinal element 1610 is rotated to expand the implant 1600 to engage the upper endplate 1620' and the lower endplate 1620" to the adjacent vertebra 1510' and 1510" through spikes 1625', 1625" or other means known in the medical arts.

It is to be understood that surface of the endplate interfacing with the vertebra can be harmonious to facilitate and promote bone ingrowth. As well known in the art, sintered metal surfaces and other porous materials have been found particularly effective for that purpose. While a detailed discussion is believed unnecessary, it will be appreciated that the attachment screws are particularly important for initial fixation and for immobilizing the implant with respect to the adjoining vertebrae so that bone ingrowth may ultimately occur, at which time the ingrowth becomes a major factor in maintaining fixation. Another major factor in achieving and maintaining fixation is the limited yieldability of the prosthesis that, by mimicking the action of the replaced components, reduces the stresses at the bone/prosthesis interfaces.

While in the foregoing we have disclosed embodiments of the invention in considerable detail, it will understood by those skilled in the art that many of these details may be varied without departing from the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Multiple embodiments are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about", "substantially", or "approximately." Similarly, the numerical values in the various ranges specified in this application, unless expressly indicated otherwise, are stated as approximations as though the minimum and maximum values within the stated ranges were both preceded by the word "about", "substantially", or "approximately." In this manner, variations above and below the stated ranges can be used to achieve substantially the same results as values within the ranges. As used herein, the terms "about", "substantially", and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about", "substantially", or "approximately" will serve to broaden a particular numerical value or range. Thus, as a general matter, "about", "substantially", or "approximately" broaden the numerical value. Also, the disclosure of ranges is intended as a continuous range including every value between the minimum and maximum values plus the broadening of the range afforded by the use of the term "about", "substantially", or "approximately". Thus, recitation of ranges of values herein are merely intended to serve as a shorthand method of referring individually to each separate value falling within the range, unless otherwise indicated herein, and each separate value is incorporated into the specification as if it were individually recited herein. To the extent that determining a given amount of variation of some the factors such as the criticality of the slit patterns, paper width differential pre- and post-expansion, paper weights and type, as well as other considerations known to those of skill in the art to which the disclosed subject matter is most closely related or the art relevant to the range or element at issue will have on the performance of the claimed subject matter, is not considered to be within the ability of one of ordinary skill in the art, or is not explicitly stated in the claims, then the terms "about", "substantially", and "approximately" should be understood to mean the numerical value, plus or minus 10%.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A spine stabilization system for attachment to vertebral bodies to restore or maintain vertebral motion and provide support to the spinal column comprising an elongated spinal element being:
   a. a tube, said tube having a hollow inside core forming an inner diameter, and an exterior wall forming an exterior diameter, said tube having
      i. a distal attachment end;
      ii. proximal attachment end; and
      iii. at least one flexible center section, said center section being positioned between said distal end and said proximal end, each of said at least one flexible center section having at least one slot with a width of about 0.075 inch to about 0.15 inch extending into said inside core in a serpentine pattern along a helical path at an angle from about 5 degrees to about 20 degrees, along said center section, said serpentine path forming a plurality of interlocking teeth around said each of said at least one flexible center section,
   b. at least two attachment members, said at least two attachment members affixing at least said proximal attachment end and said distal attachment end.

2. The spine stabilization system of claim 1 further comprising an elastomeric material at least one location from the group of filling said at least one slot, filling at least a portion of said inside core, encompassing at least a portion of said spinal element.

3. The spine stabilization system of claim 1 wherein said spinal element has a diameter ranging from about 1.0 to about 1.5 inches for replacing one or more diseased or fractured vertebra.

4. The spine stabilization system of claim 1 wherein said spinal element at said proximal attachment end and said distal attachment end have attachment members for attachment to a superior vertebra and inferior vertebra.

5. The spine stabilization system of claim 1 wherein said at least one slot has a width of about 2.5% to 20% of the diameter of said exterior diameter.

6. The spine stabilization system of claim 1 wherein said spinal element at said proximal attachment end and said distal attachment end have threaded receiving areas to receive said attachment members, one of said threaded receiving areas being a right hand thread and a second of said threaded receiving areas being a left hand thread.

7. The spine stabilization system of claim 6 wherein each of said attachment members, comprise:
   a. a threaded end cap,
   b. a threaded rod, said threaded rod being dimensioned to threadably engage with said end cap
   c. a ball end, said bail end being attached to said threaded rod,
   d. an end plate, said end plate being dimensioned to rotatably receive said ball end, and having securing member receiving areas.

8. The spine stabilization system of claim 7 wherein a first of said threaded end cap has a right hand thread and a second of said threaded end cap has a left hand thread.

9. The spine stabilization system of claim 7 wherein said securing member receiving areas are nails affixed to said end plate.

10. The spine stabilization system of claim 7 wherein said end plate surface is conducive for bone ingrowth.

11. The spine stabilization system of claim 1 wherein said slot has a ratio of amplitude of to pitch in the range of from greater than about 0.1 to about 0.8.

12. A spine stabilization system for attachment to vertebral bodies to restore or maintain vertebral motion and provide support to the spinal column comprising an elongated spinal element being:
   a. a tube, said tube said tube having a hollow inside core forming an inner diameter and an exterior wail forming an exterior diameter, said inner diameter ranging from about 15% to about 85% of said exterior diameter and having
  i. a distal attachment end;
  ii. a proximal attachment end; and
  iii. at least one flexible center section, said center section being positioned between said distal end and said proximal end, each of said at least one flexible center section having at least one slot extending in a generally helical path around and along said each of said at least one flexible center section, said slot has a width of about 2.5% to 20% of the diameter of said spinal element, said helical path has an angle from about 5 degrees to about 20 degrees and has a ratio of amplitude of to pitch in the range of from greater than about 0.1 to about 0.8
  b. at least two attachment members, a first of said at least two attachment members affixing to said proximal attachment end and a second of said at least two attachment members affixing to said distal attachment end.

13. The spinal stabilization system, of claim 12 wherein each of said at least two attachment members, comprise:
  a. a threaded end cap, a first of said threaded end cap having a right hand thread and a second of said threaded end cap having a left hand thread;
  b. a threaded rod, said threaded rod being dimensioned to threadabiy engage with said first threaded end cap and said second threaded end cap;
  c. a ball end, said ball end being attached to said threaded rod;
  d. an end plate, said end plate being dimensioned to rotatably receive said ball end, and having securing member receiving areas.

14. The spinal stabilization system of claim 13 wherein said securing member receiving areas are nails affixed to said end plate.

15. The spinal stabilization system of claim 12 further comprising an elastomeric material at least one location from the group of filling said at least one slot, filling at least a portion of said central core, encompassing at least a portion of said spinal element.

16. The method of stabilizing the spinal column comprising the step of:
  a. selecting appropriate diameter and length spinal element, said spinal element being hollow and having threaded ends and at least one slot extending in a generally helical manner, in a serpentine path, along said spinal element, said serpentine path forming a plurality of interlocking teeth,
  b. attaching a first endplate to a first end of said spinal element, said first endplate having a first threaded rod on a first side of said endplate and securing members on a second, opposing, side,
  c. attaching a second endplate to a first end of said spinal element, said first endplate having a second threaded rod on a first side of said endplate and securing members on a second, opposing, side,
  d. adjusting said endplates for minimum height,
  e. placing said spinal element in prepared cavity of spinal vertebra,
  f. rotating said spinal element to engage adjacent vertebra,
  g. securing said endplates to said vertebra.

17. The method of claim 16 further comprising the step of forming sockets within each of said threaded rod and said first side of said endplate and placing a ball within each of said sockets, said ball enabling angular rotation between said first endplate and said threaded rod and said second endplate and said second threaded rod.

18. The method of claim 16 further comprising the step of forming left hand threads on said first threaded rod and right hand threads on said second threaded rod.

* * * * *